United States Patent
Yokosawa et al.

(10) Patent No.: US 9,194,923 B2
(45) Date of Patent: Nov. 24, 2015

(54) MAGNETIC RESONANCE IMAGING DEVICE AND TRANSMITTING SENSITIVITY DISTRIBUTION CALCULATION METHOD

(75) Inventors: Suguru Yokosawa, Morioka (JP); Yo Taniguchi, Kokubunji (JP); Yoshitaka Bito, Kokubunji (JP); Yukio Kaneko, Kawaguchi (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 482 days.

(21) Appl. No.: 13/702,652

(22) PCT Filed: Jun. 6, 2011

(86) PCT No.: PCT/JP2011/062972
§ 371 (c)(1),
(2), (4) Date: Dec. 7, 2012

(87) PCT Pub. No.: WO2011/155461
PCT Pub. Date: Dec. 15, 2011

(65) Prior Publication Data
US 2013/0082708 A1    Apr. 4, 2013

(30) Foreign Application Priority Data
Jun. 9, 2010    (JP) .................................. 2010-131887

(51) Int. Cl.
*G01V 3/00*    (2006.01)
*G01R 33/341*    (2006.01)
(Continued)

(52) U.S. Cl.
CPC .............. *G01R 33/341* (2013.01); *A61B 5/055* (2013.01); *G01R 33/246* (2013.01); *G01R 33/54* (2013.01); *G01R 33/5659* (2013.01); *G01R 33/5612* (2013.01)

(58) Field of Classification Search
CPC ..................................................... G01R 33/5612
USPC .......................................... 324/309, 307, 314
See application file for complete search history.

(56) References Cited

U.S. PATENT DOCUMENTS 7,078,901 B2    7/2006 Feiweier et al.
(Continued)

FOREIGN PATENT DOCUMENTS

JP    2008-67830    3/2008
WO    WO 2005/043182 A1    5/2005

OTHER PUBLICATIONS

E. K. Insko et al., $B_1$ Mapping, Proceeding of the 11th Annual Meeting of SMRM, Berlin, Germany, 1992, pp. 4302.
(Continued)

*Primary Examiner* — Louis Arana
(74) *Attorney, Agent, or Firm* — Baker Botts L.L.P.

(57) ABSTRACT

B1 distribution is calculated in a short time with a high degree of precision, and a high quality image is obtained. In the RF shimming for irradiating electromagnetic waves using an RF coil having multiple channels, the absolute values of subtraction images between multiple reconstructed images are used to calculate a transmitting sensitivity distribution which is necessary for calculating inter-channel phase difference and amplitude ratio of RF pulses provided to the respective channels. Those multiple reconstructed images are obtained by executing the imaging sequence after applying a prepulse at different flip angles respectively. Assuming an image obtained with a minimum flip angle as a reference image, for instance, the subtraction images are created between the reference image and the other respective images. It is also possible that multiple subtraction images being obtained are divided by one another, and the transmitting sensitivity distribution is created on the basis of the division result.

11 Claims, 11 Drawing Sheets

(51) Int. Cl.
*A61B 5/055* (2006.01)
*G01R 33/565* (2006.01)
*G01R 33/54* (2006.01)
*G01R 33/24* (2006.01)
*G01R 33/561* (2006.01)

(56) References Cited

U.S. PATENT DOCUMENTS

| | | | | |
|---|---|---|---|---|
| 8,077,955 | B2* | 12/2011 | Dannels et al. | 382/131 |
| 8,324,898 | B2* | 12/2012 | Sung et al. | 324/309 |
| 8,698,495 | B2* | 4/2014 | Nehrke et al. | 324/309 |
| 2015/0015258 | A1* | 1/2015 | Fautz et al. | 324/309 |
| 2015/0042335 | A1* | 2/2015 | Nehrke et al. | 324/309 |

OTHER PUBLICATIONS

Hai-Ling Margaret Cheng et al., Rapid High-Resolution $T^1$ Mapping by Variable Flip Angles: Accurate and Precise Measurements in the Presence of Radiofrequency Field Inhomogeneity, Magnetic Resonance in Medicine 55, 2006, pp. 566-574.

J.T. Vaughan et al., 7T vs. 4T: RF Power, Homogeneity, and Signal-to-Noise comparison in Head Images, Magnetic Resonance in Medicine 46, 2001, pp. 24-30.

O.D. Leinhard et al., Whole volume three dimensional B1 in 10 seconds, Proc. Intl. Soc. Mag. Reson. Med. 16 (2008).

H. Weber et al., Extended Multi-Flip-angle approach: a 3D B1unit+mapping method for inhomogeneous fields, Proc. Intl. Soc. Mag. Reson. Med. 17 (2009).

E. K. Insko et al. Mapping of the Radiofrequency Filed, Journal of Magnetic Resonance Series A 103, 82-85 (1993).

\* cited by examiner

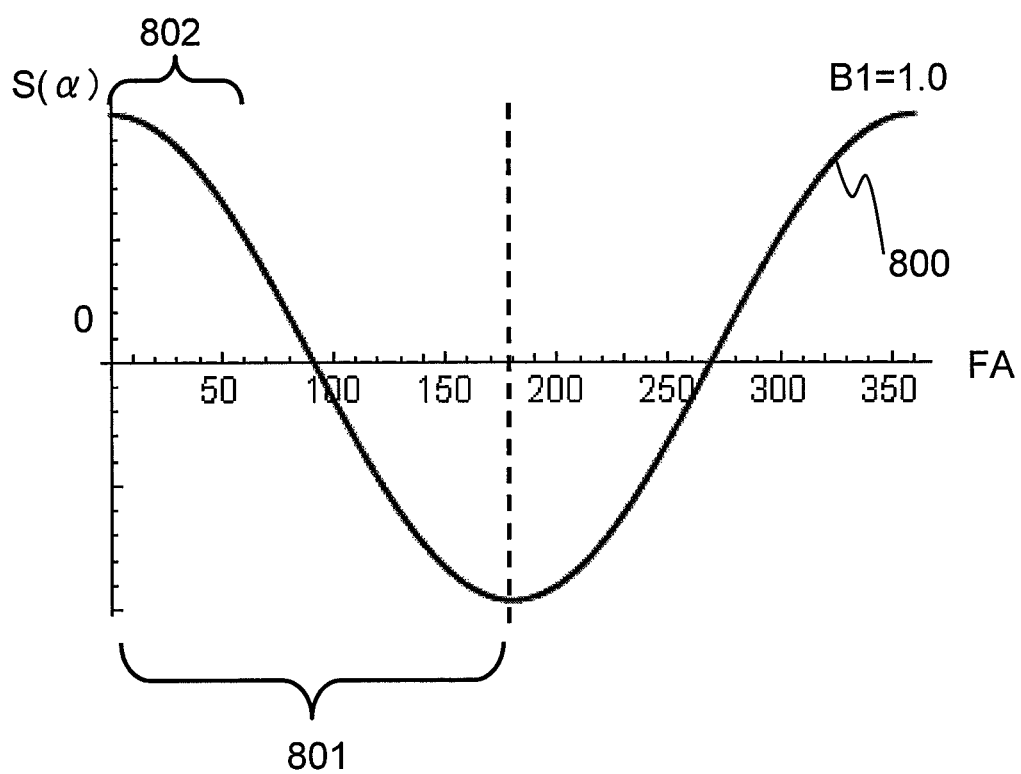

MAGNETIC RESONANCE IMAGING DEVICE AND TRANSMITTING SENSITIVITY DISTRIBUTION CALCULATION METHOD

TECHNICAL FIELD

The present invention relates to a magnetic resonance imaging apparatus (hereinafter, referred to as "MRI apparatus"), and more particularly, it relates to a technique for calculating a transmitting sensitivity distribution, the technique being used in RF shimming to reduce inhomogeneity of transmitting sensitivity in a transmit RF coil.

BACKGROUND ART

The MRI apparatus is a diagnostic imaging apparatus for medical use, utilizing nuclear magnetic resonance phenomenon due mainly to atomic nuclei of hydrogen. In general, a radio frequency magnetic field with a specific frequency is applied to a subject placed in a static magnetic field, simultaneously with a slice gradient magnetic field, thereby exciting nuclear magnetization within a cross section targeted for imaging. Next, a phase encoding gradient magnetic field and a readout gradient magnetic field are applied to provide the nuclear magnetization being excited with planar positional information, and a nuclear magnetic resonance signal generated from the nuclear magnetization is measured. The measurement of the nuclear magnetic resonance signal is repeated until filling measurement space referred to as k-space with the signals. An image is created from the signals being filled in the k-space by an inverse Fourier transform. Three types of gradient coils respectively associated with three axis directions orthogonal to one another apply the respective gradient magnetic fields. The RF magnetic field is applied by transmitting an RF pulse to the transmit radio frequency (hereinafter, referred to as "RF") coil, and irradiating electromagnetic waves. In addition, a receive RF coil is used to measure the nuclear magnetic resonance signal.

The RF pulse and each of the gradient magnetic fields are applied based on a pulse sequence being predetermined. Various pulse sequences are known for any purpose. By way of example, in the pulse sequence of a gradient echo (GrE) type, the phase encoding gradient magnetic field is made to vary sequentially for each repetition time of the pulse sequence (TR), thereby measuring the nuclear magnetic resonance signals, the number of which is required for obtaining one tomographic image.

It is possible to set the RF pulse strength arbitrarily, according to a flip angle which is an imaging parameter. Here, the flip angle of 90 degrees indicates the RF pulse strength which maximizes a nuclear magnetic resonance signal (free induction decay signal: FID signal) to be measured, and the RF pulse with the flip angle of 90 degrees is referred to as 90° pulse. The RF pulse corresponding to the flip angle of 180 degrees is referred to as 180° pulse. The strength of each gradient magnetic field being applied is calculated and configured, on the basis of imaging parameters, such as a field of view of imaging, a reception band, and a size of measurement matrix.

An RF pulse being added before the pulse sequence, aiming at modifying image contrast, is referred to as a prepulse. A typical prepulse is an inversion recovery pulse which transmits the 180° pulse prior to any pulse sequence. A time duration from transmitting the inversion recovery pulse until measuring the nuclear magnetic resonance signal at the center of the k-space is referred to as "inversion time TI", and the inversion time TI is adjusted to acquire the image contrast for any purpose.

Recently, in order to enhance the SN ratio of the image, the magnetic field in an MRI apparatus is developed to be magnetized higher, and an apparatus provided with the static magnetic field strength 3T or higher is coming into widespread use. A high magnetic field system allows acquisition of a high contrast image. On the other hand, there may occur a problem specific to this kind of high magnetic field system, that is, unevenness may occur in an abdominal image, or the like. Inhomogeneity in a rotating magnetic field which the transmit RF coil forms in an imaging region may be one of the causes of such image non-uniformity. This is called inhomogeneity in a transmitting sensitivity distribution (B1 distribution). This inhomogeneity occurs due to the reason as the following; when a magnetic resonance frequency of an electromagnetic wave to be irradiated becomes higher, along with the magnetization being higher, a wavelength of the electromagnetic wave within a living body becomes a scale almost equivalent to the size of the living body, and a phase of the electromagnetic wave is made to vary.

For reducing the inhomogeneity in the B1 distribution, there is suggested a method referred to as "RF shimming" which irradiates electromagnetic waves by using the transmit RF coil having multiple channels (e.g., see the Patent Document 1). This method controls phase and amplitude of the RF pulses provided to the respective channels, thereby reducing the inhomogeneity of the B1 distribution in the imaging region. Typically, in order to implement the RF shimming to achieve high homogeneity of the B1 distribution, the phase and amplitude provided to each of the channels are determined based on the B1 distribution created by each channel. Since the B1 distribution is dependent on the subject's body type, an organizational structure thereof, and the like, it is necessary to measure the B1 distribution for each channel as to each imaging portion of each subject.

As a typical method for measuring the B1 distribution, a double angle method is considered. This method calculates the B1 distribution by using images taken at an optional flip angle $\alpha$ and at its doubled flip angle $2\alpha$ (e.g., see the Non Patent Document 1). In addition, there is suggested another method which acquires more than one image being different in the flip angle, and subjects the image signals being acquired to the fitting according to a theoretical formula as to image signal strength, the theoretical formula being defined for each pulse sequence, thereby calculating the B1 distribution (e.g., see the Non Patent Document 2). Alternatively, there is suggested a method for calculating the B1 distribution based on a cycle of signal strength variation without performing the fitting (e.g., see the Patent Document 2). Further alternatively, there is suggested another method which takes multiple images, while gradually varying the flip angle of a prepulse for the pulse sequence to which the prepulse is added, and calculates the B1 distribution based on the cycle of the image signal strength variation (e.g., see the Non Patent Document 3).

PRIOR ART DOCUMENT

Patent Document

Patent Document 1
Specification of the U.S. Pat. No. 7,078,901
Patent Document 2
Japanese Unexamined Patent Application Publication No. 2008-067830

Non Patent Document

Non Patent Document 1
"B1 Mapping" (Insko E K, Bolinger L., In: Proceedings of the 11th Annual Meeting of SMRM, Berlin, Germany, 1992, p. 4302)

Non Patent Document 2
"Rapid High-Resolution T1 Mapping by Variable Flip Angles: Accurate and Precise Measurements in the Presence of Radiofrequency Field Inhomogeneity" (Hai-Ling Maergaret Cheng, Cgraham A Wright, Magnetic Resonance in Medicine 55: 566-574, 2006)

Non Patent Document 3
"7T vs. 4T: RF Power, Homogeneity, and Signal-to-Noise Comparison in Head Images" (J. T. Vaughan, M. Garwood, G. M. Collins, W. Liu, L. DelaBarre, G. Adriany, P. Andersen, H. Merkle, R. Goebel, M. B. Smith, and K. Ugurbil, Magnetic Resonance in Medicine 46: 24-30, 2001)

DISCLOSURE OF THE INVENTION

Problem to be solved by the Invention

In the technique disclosed by the Non Patent Document 1, it is necessary to set TR (repetition time being a transmission interval of the RF pulses) to be long, around five seconds, in order to remove effects of longitudinal relaxation time (T1) on the image signals. With this configuration, it is possible to calculate the B1 distribution according to a simple calculation formula, but this makes the measurement time longer. According to the techniques disclosed by the Non Patent Document 2 and the Patent Document 2, since a function used in the fitting includes the relaxation time, it is not necessary to remove the effects of the relaxation time, enabling measurement within a short TR. Therefore, it is possible to calculate the B1 distribution at a higher speed relative to the method disclosed by the Non Patent Document 1. However, the precision in the calculation is dependent on the number of images to be taken, and complicated calculation is further required. According to the technique disclosed by the Non Patent Document 3, the cycle of strength variation of an image signal, being a base for calculating the B1 distribution, is only dependent on the flip angle of the prepulse, and it is not affected by the pulse sequence executed subsequently. Therefore, by using the pulse sequence which has a short TR, it is possible to calculate the B1 distribution at higher speed relative to the method disclosed by the Non Patent Document 1. However, similar to the methods as disclosed by the Non Patent Document 2 and the Patent Document 2, the calculating precision is dependent on the number of images being taken and a complicated calculation is necessary.

Therefore, when the B1 distribution is tried to be calculated with a high degree of precision, the calculation takes time, whereas if the calculation is tried to be performed at a high speed, the level of precision is reduced. If it fails to calculate the B1 distribution with a high degree of precision within a limited examination time, proper RF shimming is not successfully executed, nor correcting the inhomogeneity of the B1 distribution, resulting in that image quality is deteriorated.

The present invention has been made in view of the situations above, and an object of the present invention to provide a technique to calculate the B1 distribution with a high degree of precision within a short time, so as to obtain a high quality image.

Means to solve the Problem

The present invention is directed to calculation of a transmitting sensitivity distribution by using the absolute value of a subtraction image between multiple reconstructed images, the transmitting sensitivity distribution being required for calculating inter-channel phase difference and amplitude ratio between RF pulses respectively provided to multiple channels held by an RF coil which is used in RF shimming to irradiate electromagnetic waves. The multiple reconstructed images are obtained by executing imaging sequences after applying prepulses at different flip angles respectively. An image obtained at a minimum flip angle is assumed as a reference image, and the subtraction image is created with respect to the reference image. It is further possible that multiple subtraction images being obtained are further divided by one another, and according to the result thereof, the transmitting sensitivity distribution is created.

Specifically, the present invention provides a magnetic resonance imaging apparatus, including a static magnetic field forming means for forming a static magnetic field in a space where a subject is placed, a gradient magnetic field applying means for applying a gradient magnetic field to the subject, a radio frequency magnetic field applying means having a transmission coil with multiple channels and applying a radio frequency magnetic field to the subject, a signal receiving means for receiving a nuclear magnetic resonance signal generated from the subject, a measurement control means for controlling according to a predetermined imaging sequence, operations of the gradient magnetic field applying means, the radio frequency magnetic field applying means, and the signal receiving means, thereby performing measurement, and a transmitting sensitivity shimming preparing means for calculating inter-channel phase difference and amplitude ratio of RF pulses applied from the channels respectively, so as to correct inhomogeneity of a transmitting sensitivity distribution of the transmission coil, the transmitting sensitivity shimming preparing means further including, a transmitting sensitivity measuring means for repeatedly executing an imaging sequence to which a prepulse is added while applying the prepulse at different flip angles, thereby acquiring multiple reconstructed images for the respective flip angles of the prepulse, with respect to each of the channels of the transmission coil, a transmitting sensitivity distribution calculating means for determining a reference image from the multiple reconstructed images, calculating a subtraction image between the reference image and each of the reconstructed images other than the reference image, with respect to each of the channels of the transmission coil, and calculating the transmitting sensitivity distribution by using the subtraction images being calculated, a phase difference and amplitude ratio calculating means for calculating independently, inter-channel phase difference and amplitude ratio of the RF pulses transmitted to the respective channels of the transmission coil, based on the transmitting sensitivity distribution being calculated, and a phase difference and amplitude ratio setting means for setting the phase difference and the amplitude ratio being calculated, to the measurement control means, and the measurement control means controlling the radio frequency magnetic field applying means to apply the RF pulses with the phase difference and the amplitude ratio being set, from the respective channels of the transmission coil.

The present invention further provides a transmitting sensitivity distribution calculating method for calculating a transmitting sensitivity distribution of multiple channels of a transmission coil in a magnetic resonance imaging apparatus, for applying RF pulses to a subject placed in a static magnetic field space, the method including a transmitting sensitivity measuring step of repeatedly executing an imaging sequence to which a prepulse is added while applying the prepulse at different flip angles, and acquiring multiple reconstructed images for the respective flip angles of the prepulse, with respect to each of the channels, and a transmitting sensitivity distribution calculating step of determining a reference image from the multiple reconstructed images, calculating a subtraction image between the reference image and each of the reconstructed images other than the reference image, with respect to each of the channels, and calculating a transmitting sensitivity distribution by using the subtraction images being calculated.

Effect of the Invention

According to the present invention, it is possible to calculate the B1 distribution within a short time with a high degree of precision, and obtain a high quality image.

BRIEF DESCRIPTION OF DRAWINGS

FIG. 10 illustrates an optimum selection range of flip angle according to the second embodiment;

BEST MODE FOR CARRYING OUT THE INVENTION

First Embodiment

Hereinafter, a first embodiment to which the present invention is applied will be explained. It is to be noted that the present embodiment does not restrict the scope of present invention. Hereinafter, in the entire drawings for explaining the embodiments of the present invention, constituents having the same function are labeled the same, and tedious explanations shall not be made.

Figure 1:
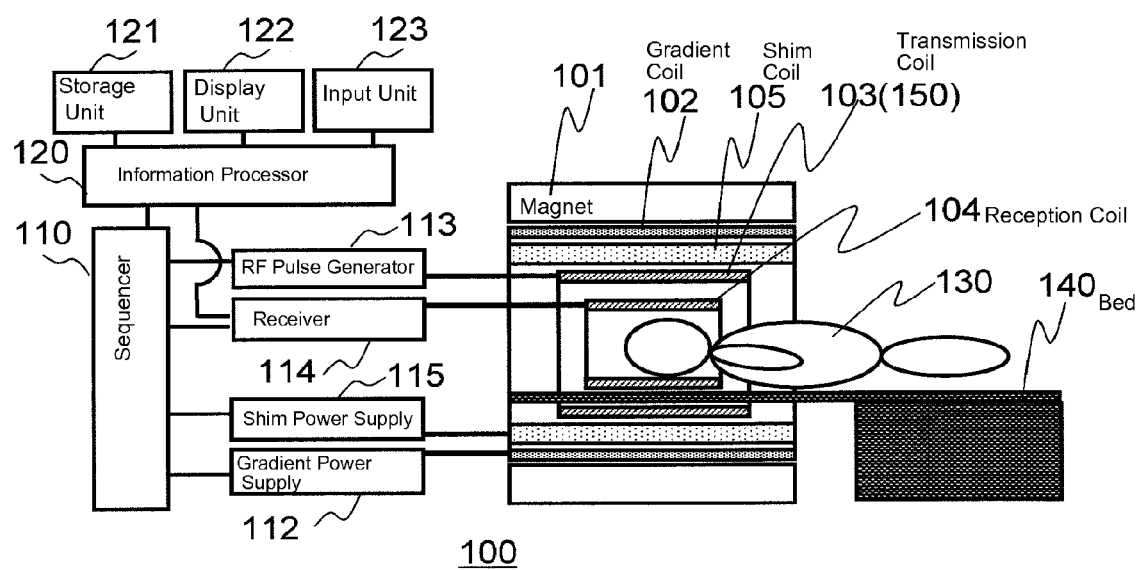
FIG. 1 is a block diagram showing a magnetic resonance imaging apparatus according to a first embodiment.

FIG. 1 is a block diagram showing a typical configuration of the magnetic resonance imaging (MRI) apparatus 100 according to the present embodiment. This MRI device is provided with a magnet 101, a gradient coil 102, a transmit RF coil (transmission coil) 103, a receive RF coil (reception coil) 104, a sequencer 110, a gradient power supply 112, an RF pulse generator 113, a receiver 114, an information processor 120, a storage unit 121, a display unit 122, an input unit 123, and a bed 140. In addition, if it is necessary to adjust homogeneity of the static magnetic field, a shim coil 105 and a shim power supply 115 are provided.

The magnet 101 forms the static magnetic field (B0) in the space where the subject 130 is placed. The subject 130 is placed on the bed (table) 140. Various types of magnet are employed as the magnet 101 depending on the structure of the MRI apparatus.

The gradient coil 102 provides gradient magnetic fields in three directions being orthogonal to one another. The gradient magnetic fields provide a nuclear magnetic resonance signal with positional information such as a slice selection, a phase encode, and a frequency encode. The gradient power supply 112 drives the gradient coil 102. The shim coil 105 is made up of multiple channels, and the shim power supply 115 supplies current to drive the shim coil.

The transmission coil 103 applies a radio frequency magnetic field to the subject 130. The RF pulse generator 113 generates an RF pulse that is transmitted to the transmission coil 103, and the radio frequency magnetic field is applied to the subject 130 placed in the static magnetic field. In the present embodiment, the transmission coil 103 is made up of multiple channels 150 being capable of controlling a phase and an amplitude of the transmitted RF pulse, independently. The sequencer 110 controls the phase and the amplitude of the RF pulse being transmitted to each of the channels 150. Hereinafter, in the present embodiment, an explanation will be made, assuming that the transmission coil 103 is made up of m channels 150. The number of channels 150 constituting the transmission coil 103 is not limited.

The reception coil 104 receives a nuclear magnetic resonance signal generated from the subject 130. The receiver 114 detects the nuclear magnetic resonance signal received by the reception coil 104. The sequencer 110 sets a nuclear magnetic resonance frequency which is assumed as a reference of detection. The nuclear magnetic resonance signal being detected is transmitted to the information processor 120. In the present embodiment, an explanation will be made taking an example that the transmission coil 103 and the reception coil 104 are used separately, but it is possible to configure one coil in such a manner as having both functions of the transmission coil 103 and the reception coil 104.

The sequencer 110 controls operations of the gradient power supply 112, the RF pulse generator 113, and the receiver 114, thereby controlling the timing for applying the gradient magnetic field and the radio frequency magnetic field and for receiving the nuclear magnetic resonance signal, the amount of application, and the like. The control of the timing is performed according to an instruction from the information processor 120, following a time chart referred to as a pulse sequence which is predefined depending on an imaging method. The storage unit 121 stores the pulse sequence in advance. The storage unit 121 further configures settings in advance, regarding detailed conditions such as a selection of the pulse sequence to be used, and each application amount. The settings above are performed by the information processor 120, or by a user via the input unit 123.

When the homogeneity of the static magnetic field is adjusted, the sequencer 110 controls the current flowing in each of the shim coils. In other words, the sequencer 110 sends a command to the shim power supply 115, and generates additional magnetic field in the shim coil 105, which allows the static magnetic field inhomogeneity to be corrected.

The information processor 120 outputs a command to the sequencer 110 according to instructions from the pulse sequence and the user, and executes imaging. In addition, various arithmetic processes are performed on the nuclear magnetic resonance signals obtained via the receiver 114, and an image is reconstructed. The information processor further calculates from the reconstructed image, a parameter to correct the inhomogeneity in the transmitting sensitivity of the transmission coil 103. The information processor 120 is connected to the receiver 114, the sequencer 110, the storage unit 121, the display unit 122, the input unit 123, and the like. The display unit 122 is an interface to display for the user, spectrum information and image information being created. The input unit 123 is an interface for the user to input a measurement condition, conditions, parameters, and the like, necessary for the arithmetic processing. The storage unit 121 records as needed, various information including the reconstructed image generated by the information processor 120, information, and the like, inputted via the input unit 123, and the pulse sequence, and the like.

It is to be noted that the information processor 120 is provided with a CPU and a memory. The CPU loads on the memory, programs stored in the storage unit 121, and the like, and executes those programs, thereby implementing various functions of the information processor 120.

Figure 2:
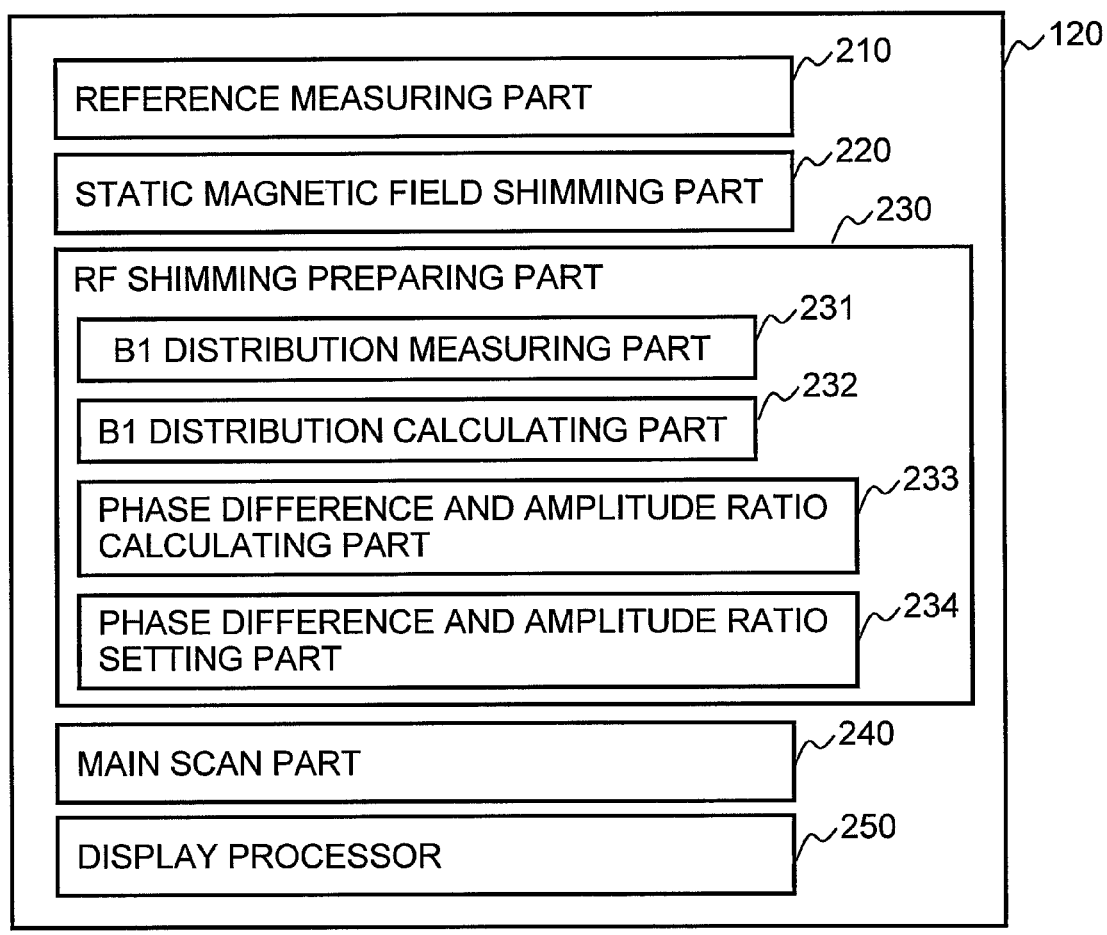
FIG. 2 is a functional block diagram showing an information processor according to the first embodiment.

As described above, the information processor 120 of the present embodiment controls the constituent elements of the MRI apparatus 100, corrects inhomogeneity of the static magnetic field and the transmitting sensitivity, and executes the main scan. In order to implement the processing above, as shown in FIG. 2, the information processor 120 of the present embodiment is provided with a reference measuring part 210 for executing the reference measurement, a static magnetic field shimming part 220 for performing static magnetic field shimming, an RF shimming preparing part 230 for calculating parameters for the RF shimming and setting the parameters in the sequencer 110, an main scan part 240 for executing the main scan, and a display processor 250 for reconstructing an image from the nuclear magnetic resonance signals obtained by the main scan and displaying the reconstructed image on the display unit 122.

Figure 3:
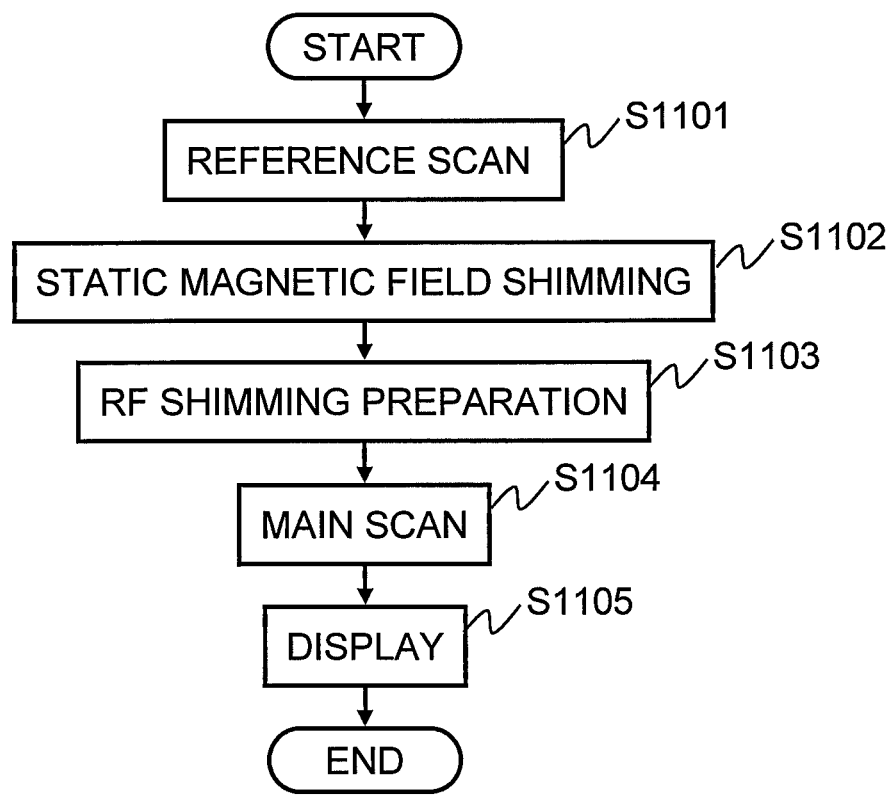
FIG. 3 is a flowchart showing an imaging process according to the first embodiment.

Firstly, an explanation will be made as to an overview of the processing flow upon imaging performed by each constitutional element above, and thereafter, details of the processing of each element will be further explained. FIG. 3 is a processing flow of the imaging process when the MRI apparatus 100 of the present embodiment takes an image of the subject 130. The imaging process is started according to an instruction from the user to start imaging, or according to a program registered in advance.

Upon accepting an instruction to start examination, the reference measuring part 210 firstly executes a reference scan to prepare for the imaging (step S1101). Next, the static magnetic field shimming part 220 performs measurement for static magnetic field (B0) shimming, calculates a B0 distribution, and adjusts a shim current value for correcting the static magnetic field inhomogeneity (static magnetic field shimming process; step S1102). Next, the RF shimming preparing part 230 performs measurement for calculating a transmitting sensitivity (B1) distribution, calculates a B1 distribution, calculates a parameter for correcting the transmitting sensitivity, and set the parameter in the sequencer 110 (RF shimming preparation process; step S1103). In here, inter-channel phase difference and amplitude ratio of an RF pulse provided to each channel 150 (hereinafter, referred to as phase difference and amplitude ratio) are determined, and these are set in the sequencer 110. Then, the main scan part 240 executes main scan for any examination purpose (step S1104). On this occasion, the sequencer 110 instructs the RF pulse generator 113 to transmit RF pulses to the respective channels 150, keeping the phase difference and the amplitude ratio set by the RF shimming preparing part 230. The display processor 250 displays a reconstructed image obtained by the main scan on the display unit 122 (step S1105).

The imaging process above is repeated every time when the subject is changed, or every time when an imaging target portion is changed even though the subject 130 is unchanged.

Hereinafter, detailed explanations will be made as to each of the steps of the imaging process as shown in FIG. 3.

The reference measuring part 210 executes a pre-scan, a scout scan, and the like, as the reference scan of the step S1101. The pre-scan is carried out aiming at adjusting a center frequency, irradiation power of the RF pulse, and a reception gain. The scout scan is carried out aiming at identifying the position of the subject 130. The reference measuring part 210 outputs an instruction to the sequencer 110 according to a predetermined pulse sequence, and executes each of the reference scans. If those information items have already been acquired, it is not necessary to perform the reference scans. On this occasion, it is not necessary to provide the reference measuring part 210.

Next, an explanation will be made as to the static magnetic field (B0) shimming process performed by the static magnetic field shimming part 220 in the step S1102. The static magnetic field shimming part 220 determines a value of current to be supplied to the shim coil 105, so as to correct the static magnetic field inhomogeneity. A current value being calculated is transferred to the sequencer 110, and it is outputted from the shim power supply 115 according to an instruction from the sequencer 110. The shim coil 105 generates a magnetic field according to the current supplied from the shim power supply 115, thereby correcting the inhomogeneity of the static magnetic field (B0). If there is no inhomogeneity in the static magnetic field, this static magnetic field shimming process is not necessarily performed. In this case, it is not necessary to provide the static magnetic field shimming part 220.

In order to determine the current value as described above, the static magnetic field shimming part 220 firstly measures the static magnetic field distribution (B0 distribution). For measuring the B0 distribution, the static magnetic field shimming part 220 executes the measurement according to two GrE (gradient echo) type pulse sequences, which are different in echo time TE. The static magnetic field shimming part 220 outputs an instruction to the sequencer 110, according to the GrE type pulse sequences held in advance, thereby executing this measurement.

Then, the static magnetic field shimming part 220 reconstructs images respectively based on the nuclear magnetic resonance signals obtained from those pulse sequences.

Next, the static magnetic field shimming part 220 calculates a phase difference between thus obtained two reconstructed images. The static magnetic field shimming part 220 uses the obtained phase difference, to create a distribution of the static magnetic field distribution being biased (static magnetic field inhomogeneity) $\Delta B0$.

The following formula (1) expresses the static magnetic field inhomogeneity ΔB0, using a phase difference ΔΦ between the images, TE time difference ΔT, and a nuclear gyromagnetic ratio γ:

[Formula 1]

$$\Delta B0 = \Delta \Phi / (\gamma \cdot \Delta T) \quad (1)$$

The static magnetic field shimming part 220 uses the formula (1) to obtain the static magnetic field inhomogeneity of each pixel, thereby creating the static magnetic field inhomogeneity distribution. Then, on the basis of thus created distribution, the static magnetic field shimming part 220 calculates a value of current to be supplied to the shim coil 105. The current value being calculated is set in the sequencer 110, and according to the instruction from the sequencer 110, the shim power supply 115 outputs the current of this value.

In addition, the static magnetic field shimming part 220 may be configured such that it obtains the static magnetic field inhomogeneity distribution after the correction, according to a computation. It is also possible to configure the static magnetic field inhomogeneity distributions before and after applying the correction in the form of display images, and display them on the display unit 122. This configuration allows the operator to verify the changes in the static magnetic field distribution caused by the B0 shimming process.

Next, an explanation will be made as to the RF shimming preparation process executed by the RF shimming preparing part 230 in the step S1103. The RF shimming preparing part 230 calculates a transmitting sensitivity distribution (B1 distribution), being a distribution of rotating magnetic field strength that is formed in the imaging region by the transmission coil 103, calculates inter-channel phase difference and amplitude ratio of the RF pulses transmitted to the respective channels 150, so as to correct the inhomogeneity of the distribution, and sets those calculated results in the sequencer 110. In order to implement the processing above, as shown in FIG. 2, the RF shimming preparing part 230 is provided with a B1 distribution measuring part 231, a B1 distribution calculating part 232, a phase difference and amplitude ratio calculating part 233, a phase difference and amplitude ratio setting part 234. With the functions as described above, the phase difference and the amplitude ratio being calculated are set in the sequencer 110. The sequencer 110 sends an instruction to the RF pulse generator 113, in such a manner that the RF pulses are generated with thus set phase difference and amplitude ratio and transmitted to the respective channels 150 in the measurement subsequently performed.

Figure 4:
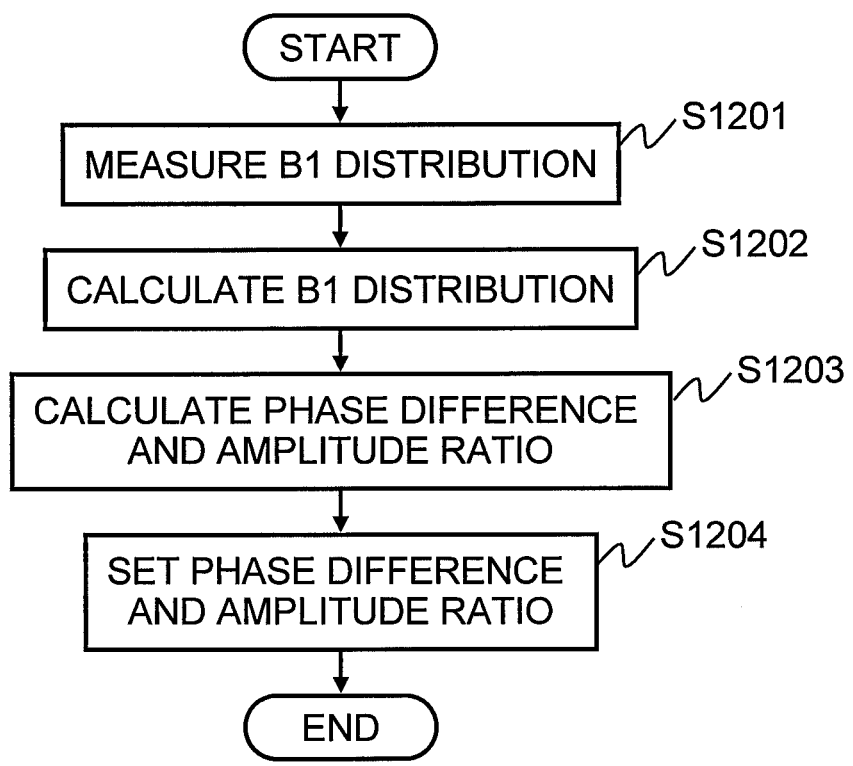
FIG. 4 is a flowchart showing an RF shimming preparation process according to the first embodiment.

FIG. 4 is a processing flow showing the RF shimming preparation process executed by each part in the RF shimming preparing part 230 according to the present embodiment. As shown in this figure, the B1 distribution measuring part 231 firstly performs measurement (B1 distribution measurement) for calculating the B1 distribution of each of the channels 150, and acquires reconstructed images (step S1201). Then, the B1 distribution calculating part 232 uses the reconstructed images to perform the B1 distribution calculating process, thereby calculating the B1 distribution in each of the channels 150 (step S1202). Then, on the basis of thus obtained B1 distributions, the phase difference and amplitude ratio calculating part 233 performs the phase difference and amplitude ratio calculating process for calculating the phase difference and the amplitude ratio of the RF pulses transmitted to the respective channels 150 (step S1203). Then, the phase difference and amplitude ratio setting part 234 sets in the sequencer 110, thus calculated inter-channel phase difference and the amplitude ratio of the RF pulses that are transmitted to the respective channels 150 (step S1204). Hereinafter, detailed explanations will be made as to each of the processes.

Figure 5:
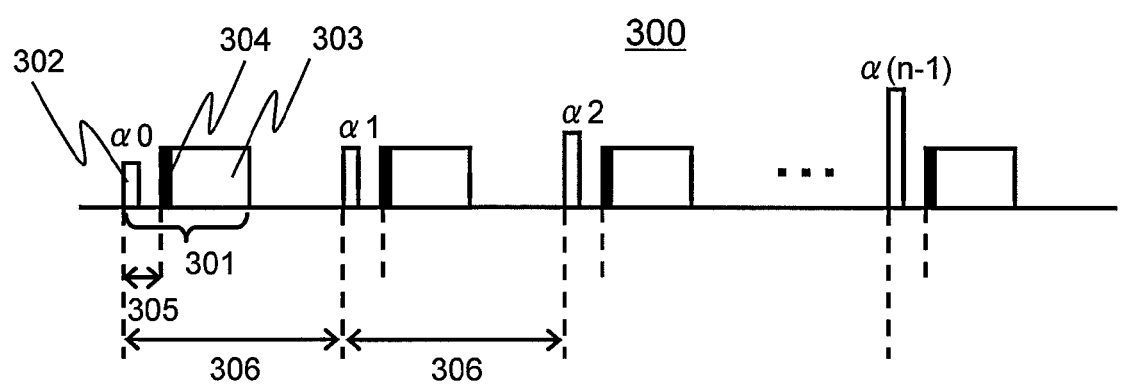
FIG. 5 illustrates a sequence that is used in the first embodiment.

Firstly, the B1 distribution measurement performed by the B1 distribution measuring part 231 in the step S1201 will be explained. The B1 distribution measuring part 231 executes a predetermined imaging sequence more than once, each adding a prepulse being different in flip angle, and obtains reconstructed images for the respective flip angles. On this occasion, at least three types of flip angles are used, being different from one another. FIG. 5 illustrates the sequence 300 that is used in the B1 distribution measurement of the present embodiment. The horizontal axis in the figure represents a time axis. The B1 distribution measuring part 231 sends an instruction to the sequencer 110 according to the sequence 300, and executes the measurement for calculating the B1 distribution.

The sequence 300 is provided with segments 301 having a constant time interval 306 (hereinafter referred to as "TD") and repeated n times (n is an integer at least three). Each segment 301 is provided with a prepulse 302 and an imaging sequence 303.

The prepulse 302 indicates one RF pulse (prepulse) that is settable at any flip angle. The flip angle of the prepulse 302 is made to vary for each repetition of the segment 301. Hereinafter, the flip angle at each time is assumed as $\alpha 0, \alpha 1, \ldots,$ and $\alpha(n-1)$. Application of the prepulse 302 is followed by the application of gradient magnetic field for saturating the transverse magnetization. It is to be noted that when the prepulse 302 is applied, a slice selective gradient magnetic field is not applied.

Any type of sequence may be employed as the imaging sequence 303. By way of example, there is employed a GrE type pulse sequence whose flip angle is set to be low. Imaging parameters may also be set arbitrarily. In each segment 301, a time interval 305 from applying the prepulse 302 to the timing 304 for measuring the nuclear magnetic resonance signal at the center of the k-space in the imaging sequence 303, is assumed as TI.

As described above, in the present embodiment, the B1 distribution measuring part 231 applies the prepulses 302 having different flip angles of n types, acquires nuclear magnetic resonance signals necessary for image reconstruction, and obtains n reconstructed images. The B1 distribution measuring part 231 executes the B1 distribution measurement m times, according to the sequence 300, while driving m channels 150 independently. Accordingly, the B1 distribution measuring part 231 obtains n×m reconstructed images as a result of the B1 distribution measurement of the present embodiment.

Figure 6:
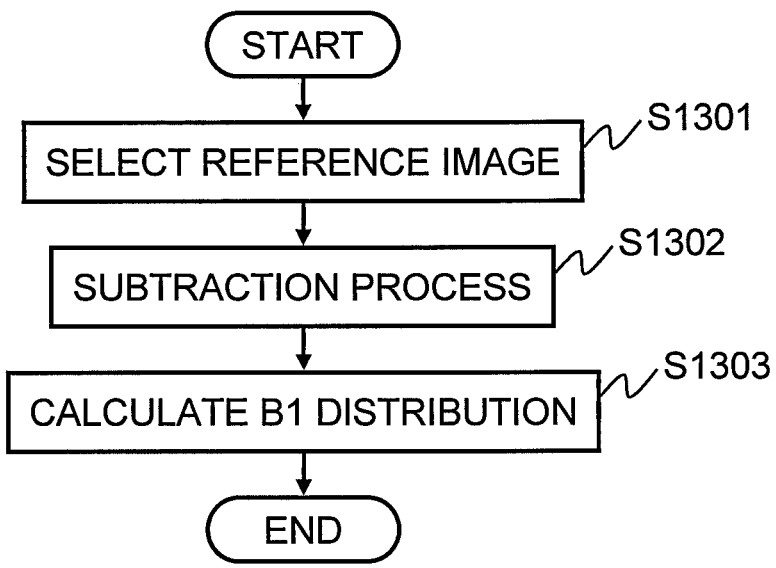
FIG. 6 is a flowchart of the B1 distribution calculating process according to the first embodiment.

Next, an explanation will be made as to the B1 distribution calculating process according to the B1 distribution calculating part 232 in the step S1202. FIG. 6 shows an overview of the B1 distribution calculating process according to the B1 distribution calculating part 232. The following process is performed for each of the channels 150.

As illustrated, the B1 distribution calculating part 232, firstly selects a reference image out of n reconstructed images obtained by the B1 distribution measurement of the channel 150 (step S1301). The reference image may be anyone of the reconstructed images, and an image having the prepulse 302 with the minimum flip angle α is desirable, for instance.

Next, the B1 distribution calculating part 232 performs a subtraction process for generating a subtraction image between the reference image and each of the remaining (n−1)

reconstructed images (step S1302). The subtraction process is performed by using complex image data including phase information.

Then, the B1 distribution calculating part 232 uses thus created (n−1) subtraction images to calculate the B1 distribution (step S1303). The B1 distribution causes a change in a cycle of signal strength variation in association with the flip angle α. By the use of this change, a B1 value of each pixel is obtained, thereby calculating the B1 distribution. Hereinafter, details of the B1 distribution calculating process according to the present embodiment will be explained.

Firstly, an explanation will be made as to the signal strength of the reconstructed image acquired by the B1 distribution measurement according to the sequence 300. In here, one pixel of the reconstructed image acquired in a certain segment 301 of the sequence 300 is focused on for the explanation. When the flip angle of the prepulse 302 applied in this segment 301 is represented as α, variation in the signal strength by the imaging sequence 303 is represented by $S_{seq}$ (a function dependent on T1, T2, TR, TE, flip angle, and the like), a longitudinal relaxation time of a proton existing in the imaging region associated with the pixel is represented as T1, and the transmitting sensitivity distribution is represented as B1, the signal strength of the target pixel S(α) is expressed by the following formula (2). In addition, the formula (2) is able to be modified as the formula (2)′:

[Formula 2]

$$S(\alpha) = S_{seq}\left(1 - (1 - \cos(B1 \cdot \alpha))e^{-\frac{TI}{T1}}\right) \quad (2)$$

$$= S_{seq}e^{-\frac{TI}{T1}}\cos(B1 \cdot \alpha) + S_{seq}\left(1 - e^{-\frac{TI}{T1}}\right)$$

Here, if $S_{seq} = A$, $S_{seq}\left(1 - e^{-\frac{TI}{T1}}\right) = C$ $$S(\alpha) = A\cos(B1 \cdot \alpha) + C \quad (2)'$$

Figure 7:
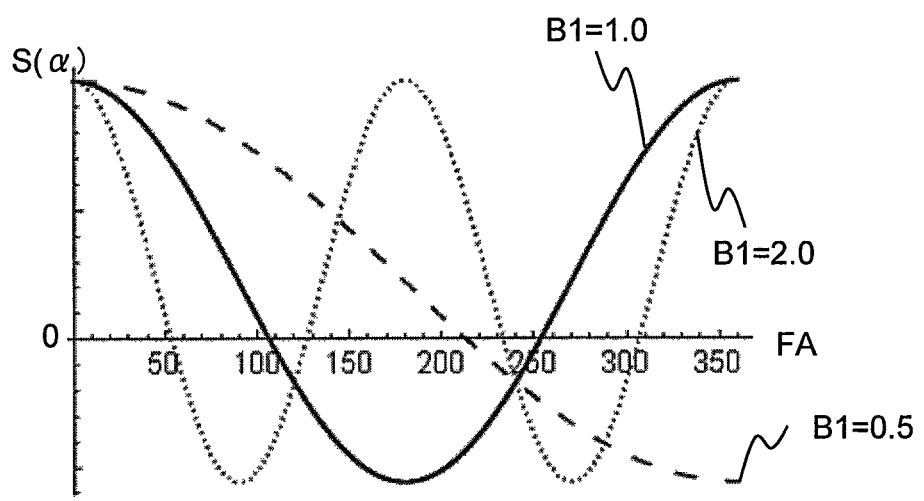
FIG. 7 is a graph showing pixel signal strength plotted for each value of B1, with respect to each flip angle of the prepulse according to the first embodiment.

According to the formula (2)′, B1 changes the variation cycle of the signal strength S(α) of the target pixel associated with the flip angle α. FIG. 7 illustrates that the signal strength S(a) of the target pixel associated with the flip angle α is plotted on the basis of the formula (2)′. The horizontal axis shows the flip angle (FA) α of the prepulse 302, and the vertical axis shows the signal strength S(α) of the target pixel. The value of B1 is assumed as 0.5, 1.0, and 2.0. The negative signal strength plotted in the figure corresponds to a signal that is shifted by π phase, relative to the phase of positive signal strength.

For example, the minimum flip angle is assumed as α0, and an image obtained by applying the prepulse 302 with the flip angle α0 is assumed as the reference image. On this occasion, the signal strength S(αi)−S(α0) of the target pixel of each subtraction image, as to each of the remaining reconstructed images (flip angle αi (i is an integer satisfying 1≤i≤n−1)) is expressed by the formula (3) as the following:

[Formula 3]

$$S(\alpha i) - S(\alpha 0) = S_{seq}(\cos(B1 \cdot \alpha i) - \cos(B1 \cdot \alpha 0))e^{-\frac{TI}{T1}} \quad (3)$$

Figure 8A:
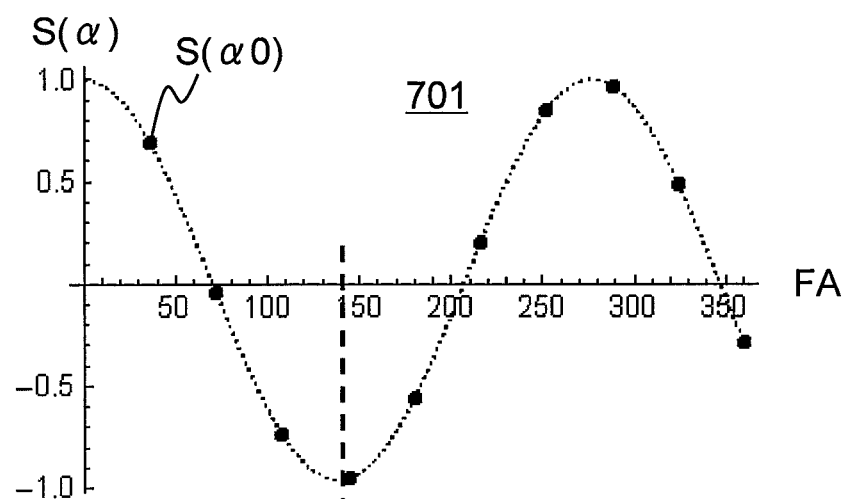
FIG. 8A is a graph showing the pixel signal strength obtained by executing the sequence according to the first embodiment, being plotted with respect to each flip angle of the prepulse.
Figure 8B:
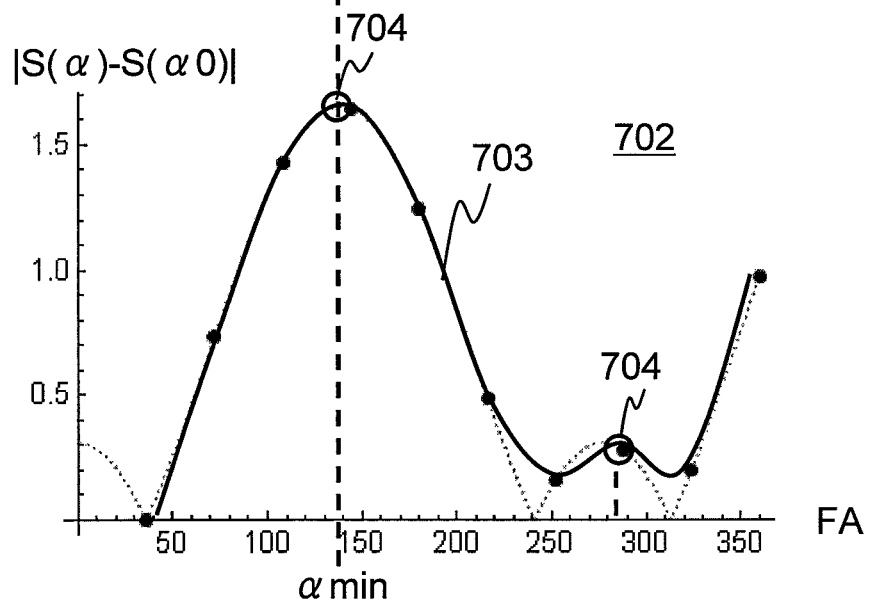
FIG. 8B illustrates a process for obtaining an approximate function, based on the result of plotting the absolute value of a difference value of the signal strength with respect to each flip angle of the prepulse.

FIG. 8A shows a result of plotting (signal strength graph) 701 which plots the signal strength of the target pixel of n reconstructed images obtained by the B1 distribution measurement of the present embodiment, on the coordinate system setting the pre pulse flip angle (FA) for the horizontal axis, and setting the signal strength S(α) for the vertical axis. Here, there is shown the case, for instance, where the flip angle of the prepulse 302 is changed ten times, and ten reconstructed images are obtained. FIG. 8B shows a result of plotting 702 which plots the absolute values of the signal strength of the target pixels in the subtraction images obtained according to the formula (3), similarly on the coordinate system setting the prepulse flip angle (FA) for the horizontal axis, and setting the absolute value of the signal strength |S(α)−S(α0)| for the vertical axis. Here, plotting is performed also for the case where α is equal to α0 (i.e., |S(α0)−S(α0)|=0).

As shown in FIG. 8A and FIG. 8B, the minimum flip angle αmin among the flip angles at which the approximate expression of the plot result 702 indicates a maximum value, the expression showing variation of absolute value of the signal strength of the subtraction images, corresponds to the flip angle after a half-cycle change in the signal strength graph 701 shown in FIG. 8A. The B1 distribution calculating part 232 utilizes this result to calculate the B1.

Specifically, the B1 distribution calculating part 232 firstly determines the approximate function 703 for the variation of the absolute value of the subtraction image, based on the plot result 702 as shown in FIG. 8B. The approximate function is determined by applying a fitting to the plot result 702. The fitting is carried out according to spline fitting that makes approximations zone by zone. It is to be noted that the segment 301 is repeated using at least three different types of flip angle, because it is intended to obtain the approximate function 703 according to this fitting.

Next, the B1 distribution calculating part 232 calculates a maximum value 704 in the approximate function 703 thus determined. It further calculates the flip angle αmin which is the minimum among the flip angles of the prepulse 302 in association with the calculated maximum value 704.

Then, the B1 distribution calculating part 232 uses amin being obtained to calculate the B1 value of the target pixel, according to the following formula (4):

[Formula 4]

$$B1 = \frac{\pi}{\alpha\min} \quad (4)$$

The B1 distribution calculating part 232 performs the processing above as to each pixel to calculate the B1 value of each pixel, and consequently obtains the B1 distribution. It is to be noted that a method for calculating the B1 distribution is not limited to this example. Furthermore, the calculation of the B1 distribution is carried out for each of m channels 150, in the same manner as the measurement for calculating the B1 distribution as described above.

Next, an explanation will be made as to the phase difference and amplitude ratio calculating process of the aforementioned step S1203, performed by the phase difference and amplitude ratio calculating part 233. The phase difference and amplitude ratio calculating part 233 calculates interchannel phase difference and amplitude ratio of the RF pulses transmitted to the respective channels 150, based on the B1 distribution being calculated. This calculation is performed according to the least square method, for instance. Specifically, when an ideal B1 distribution is represented as m, the B1 distribution of each channel 150 is represented as A, and the phase difference and the amplitude ratio of the RF pulses in the respective channels 150 are represented as x, these establish a determinant relationship as shown in the following formula (5):

[Formula 5]

$$m = Ax \qquad (5)$$

It is assumed here that the elements of the ideal B1 distribution m, are all the same values. According to the least square method, an optimum value of x satisfying the formula (5) is obtained.

Then, in the step S1204, the phase difference and amplitude ratio setting part 234 sets in the sequencer 110, the inter-channel phase difference and amplitude ratio of the RF pulses transmitted to the respective channels 150, being obtained by the phase difference and amplitude ratio calculating part 233. The sequencer 110 instructs the RF pulse generator 113 to transmit the RF pulses to the respective channels 150, with the phase difference and the amplitude ratio being set, in the subsequent imaging. The B1 shimming is carried out according to the procedure above.

Next, an explanation will be made as to execution of the main scan by the main scan part 240 in the step S1104. The main scan part 240 executes the main scan according to the pulse sequence determined by the operator for any examination purpose. On this occasion, the sequencer 110 instructs the RF pulse generator 113 to transmit the RF pulses to the respective channels 150, with the phase difference and amplitude ratio set by the RF shimming preparing part 230. Then, the RF pulse generator 113 generates the respective RF pulses having the phase difference and the amplitude ratio as instructed, and applies the RF pulses from the respective channels 150 to the subject 130. This allows acquisition of an image from which the B1 inhomogeneity is reduced.

As explained above, according to the present embodiment, the B1 distribution is calculated by using the subtraction images, between the reference image and multiple reconstructed images obtained by executing the pulse sequence to which the prepulse is added, while the flip angle of the prepulse being made to vary in a stepwise manner. By applying fitting to the absolute values of the signal strength of the subtraction images, a variation cycle of the signal strength is determined, thereby calculating the B1 distribution. Then, a difference value of the complex data is used as the signal strength of the subtraction image. Therefore, according to the present embodiment, a treatment for signal aliasing is not necessary any more, which is required in calculating the B1 distribution according to a conventional functional fitting. This reduces an error caused by a noise and allows calculation of the B1 distribution stably with a high degree of precision.

According to the present embodiment, a highly precise B1 distribution is used to calculate the inter-channel phase difference and amplitude ratio of the RF pulses transmitted to the respective channels, thereby enabling highly precise B1 shimming. Therefore, B1 correction is performed with a high degree of precision, allowing a high quality image to be obtained.

Further according to the present embodiment, the variation cycle of the image signal strength being a basis for calculating the B1 distribution is dependent only on the flip angle of the prepulse, and it is free of the influence of the pulse sequence which is executed subsequently. Accordingly, it is possible to employ a pulse sequence with a short TR. Therefore, the B1 distribution can be calculated within a short time with a high degree of precision.

According to the present embodiment, a high quality image can be obtained within a short time.

In the present embodiment, the angle to be set as the flip angle of the prepulse 302 is not particularly restricted, but the minimum flip angle may be 0 degree. On this occasion, an image being reconstructed from the result of executing the segment 301, assuming the flip angle of the prepulse 302 as zero degree, is used as the reference image. The signal strength of the target pixel in the situation above is expressed by the following formula (6):

[Formula 6]

$$S(\alpha) - S(0) = -S_{seq}(1 - \cos(B1 \cdot \alpha))e^{-\frac{TI}{T1}} \qquad (6)$$

Here, since $(1-\cos(B1 \cdot \alpha)) > 0$, if the formula (6) is employed, the B1 distribution can be calculated according to the fitting by a function which does not treat aliasing, without using the absolute value. Therefore, by setting the minimum flip angle to be zero degree, the effect similar to that of the present embodiment can be obtained according to more simplified calculation.

Second Embodiment

Next, an explanation will be made as to a second embodiment to which the present invention is applied. The MRI apparatus of the present embodiment has basically the same configuration as the MRI apparatus of the first embodiment. In the present embodiment, when the RF shimming preparing part calculates the B1 distribution, a division process is performed in addition to the subtraction process. Hereinafter, with regard to the present embodiment, an explanation will be made focusing attention on the RF shimming preparation process performed by the RF shimming preparing part, which is different from that of the first embodiment. Similar to the first embodiment, the RF shimming preparing part 230 of the present embodiment is also provided with the B1 distribution measuring part 231, the B1 distribution calculating part 232, the phase difference and amplitude ratio calculating part 233, and the phase difference and amplitude ratio setting part 234.

The B1 distribution measurement of the present embodiment is performed by using the sequence 300 basically the same as that of the first embodiment. The B1 distribution measurement of the present embodiment also repeats the segment 301 at least three times, while the flip angle of the prepulse 302 is made to vary for each time. This is configured as such in order that subtraction images are created from reconstructed images, and further the subtraction images thus obtained are divided by one another. Hereinafter, taking as an example the situation where the segment 301 is repeated three times, an explanation will be made as to the RF shimming preparation process that is performed by the RF shimming preparing part 230 of the present embodiment. The flip angle of prepulse 302 for each repetition is assumed as α0, α1, and α2. Similar to the first embodiment, prior to the RF shimming preparation process, the static magnetic field shimming, and the like, are executed, and it is assumed that the static magnetic field is in the homogeneous state.

Firstly, similar to the step S1201 of the first embodiment, the B1 distribution measuring part 231 performs measurement for calculating the B1 distribution, and acquires reconstructed images from the results, respectively. Each signal strength of the reconstructed images respectively obtained with the flip angles α0, α1, and α2, is assumed as S(α0), S(α1), and S(α2).

Figure 9:
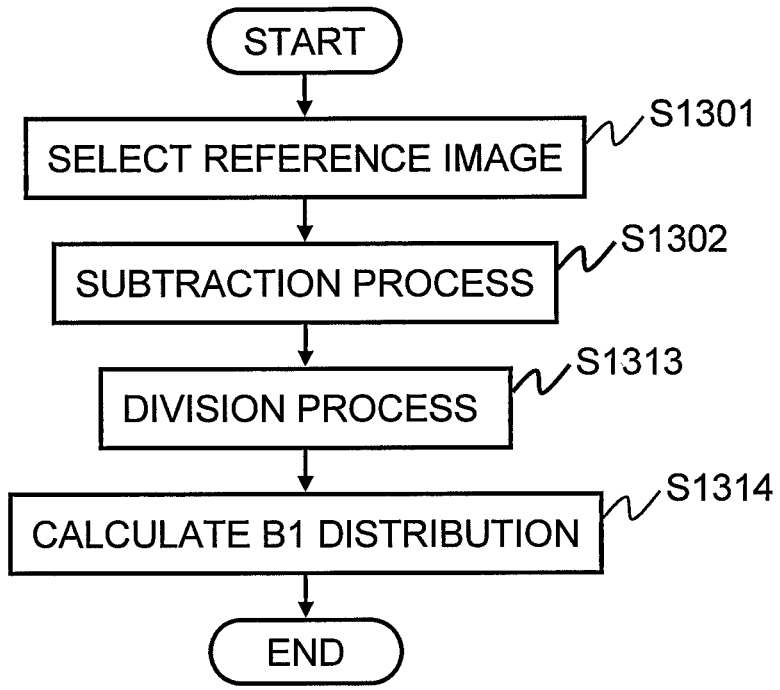
FIG. 9 is a flowchart of the B1 distribution calculating process according to a second embodiment.

Next, the B1 distribution calculating part 232 performs the B1 distribution calculating process. The B1 distribution calculating process of the present embodiment will be explained with reference to FIG. 9. FIG. 9 is a processing flow of the B1 distribution calculating process performed by the B1 distribution calculating part 232 of the present embodiment. The following process is performed with respect to each of the channels 150.

Firstly, similar to the first embodiment, the B1 distribution calculating part 232 selects a reference image from the multiple reconstructed images obtained by the B1 distribution measurement for the channel 150 (step S1301). In here, an image is selected as the reference image out of three reconstructed images, the image to be selected being acquired by applying the prepulse 302 with the minimum flip angle α0. Also in the present embodiment, the reference image may be any of the reconstructed images, but the image with the minimum flip angle α of the prepulse 302 is desirable.

When the reference image is determined, similar to the first embodiment, the B1 distribution calculating part 232 performs the subtraction process to create subtraction images between the reference image and the other multiple reconstructed images, respectively (step S1302). The signal strength of each target pixel of each of the subtraction images is expressed by the following formulas (7) and (8), according to the formula (2). Hereinafter, the subtraction image whose signal strength of the target pixel is expressed by the formula (7) is referred to as "a first subtraction image", and the subtraction image whose signal strength of the target pixel is expressed by the formula (8) is referred to as "a second subtraction image".

[Formula 7]

$$S(\alpha 1) - S(\alpha 0) = S_{seq}(\cos(B1 \cdot \alpha 1) - \cos(B1 \cdot \alpha 0))e^{-\frac{TI}{T1}} \quad (7)$$

[Formula 8]

$$S(\alpha 2) - S(\alpha 0) = S_{seq}(\cos(B1 \cdot \alpha 2) - \cos(B1 \cdot \alpha 0))e^{-\frac{TI}{T1}} \quad (8)$$

Next, the B1 distribution calculating part 232 divides the second subtraction image by the first subtraction image, thereby performing the division process to obtain a division image (step S1313). The first subtraction image may be divided by the second subtraction image. The division image is expressed by the following formula (9):

[Formula 9]

$$\frac{S(\alpha 2) - S(\alpha 0)}{S(\alpha 1) - S(\alpha 0)} = \frac{\cos(B1 \cdot \alpha 2) - \cos(B1 \cdot \alpha 0)}{\cos(B1 \cdot \alpha 1) - \cos(B1 \cdot \alpha 0)} \quad (9)$$

Then, the B1 distribution calculating part 232 calculates B1 of each pixel by using the formula (9). The formula (9) is a nonlinear equation in which $S_{seq}$ and T1 being the unknowns in the formula (2) are removed. Therefore, the B1 distribution calculating part 232 solves this nonlinear equation and calculates the B1 value of each pixel. As described above, according to the present embodiment, it is possible to calculate B1 without the fitting process. The B1 distribution calculating part 232 calculates B1 for each pixel, and then obtains the B1 distribution (step S1314).

When the B1 distribution is calculated according to the procedure above, similar to the step S1203 of the first embodiment, the phase difference and amplitude ratio calculating part 233 uses thus calculated B1 distribution to perform the phase difference and amplitude ratio calculating process, and calculates the inter-channel phase difference and amplitude ratio of the RF pulses that are transmitted to the respective channels 150.

As described above, according to the present embodiment, three images are selected out of the results obtained by repeating the segment 301 at least three times while varying the flip angle of the prepulse 302 for each time. Then, those images are subjected to the aforementioned subtraction process and division process, thereby allowing the $S_{seq}$ and T1 being unknown in the formula (2) to be removed therefrom, and deriving a function only relating to the B1 distribution as shown in the formula (9). Therefore, the B1 distribution is calculated just by solving the nonlinear equation as shown in the formula (9), enabling simplification of the computation of the B1 distribution calculating process.

Since the fitting calculation is not performed in the present embodiment, it is possible to reduce the calculation time and also improve the precision of the result. Therefore, in addition to the effect obtained by the first embodiment, the B1 distribution can be obtained with a higher degree of precision at a high speed, enhancing the image quality being obtained.

Also in the present embodiment similar to the first embodiment, zero degree may be selected as the flip angle α0 of the prepulse 302 of the segment 301 for obtaining the reference image. It is further possible to set α2 as a value doubling α1, in such a manner as setting the angles, 0 degree, 90 degrees, and 180 degrees, for instance.

On this occasion, the formula (9) may be modified as the following formula (10):

[Formula 10]

$$\frac{S(\alpha 2) - S(\alpha 0)}{S(\alpha 1) - S(\alpha 0)} = 2(1 + \cos(B1 \cdot \alpha)) \quad (10)$$

If it is assumed that α1=α in the formula (10), the target pixel B1 can be calculated according to the following formula (11):

[Formula 11]

$$B1 = \arccos\left(\frac{S(2\alpha) - S(0)}{2(S(\alpha) - S(0))} - 1\right) \Big/ \alpha \quad (11)$$

As thus described, if the flip angle of the prepulse 302 of each segment 301 is set to be 0 degree, α, and 2α (e.g., 0 degree, 90 degrees, and 180 degrees), it is possible to calculate the B1 distribution only by calculating a trigonometric function as shown in the formula (11). Therefore, the B1 distribution can be obtained at a higher speed with a higher degree of precision. Accordingly, it is possible to obtain a higher quality image.

In the present embodiment, the segment 301 is executed at least three times, while setting the flip angle of the prepulse to be different values for each time, thereby calculating the B1 distribution. According to the Nyquist's theorem, when a certain frequency is separated, at least two samples are necessary for one cycle. Therefore, in order to precisely calculate the B1 distribution, the flip angle of the prepulse of each segment 301 is set in such a manner as satisfying this theorem.

By way of example, when the B1 measurement is executed to calculate the B1 distribution, assuming the flip angle of the prepulse 302 as the following three types; 0 degree (the first flip angle), α (the second flip angle), and 2α (the third flip angle) as described above, the second flip angle α is selected from the range as described below. FIG. 10 illustrates the range for selecting the second flip angle α. In this figure, the signal strength S(α) variation 800 of the target pixel with respect to the flip angle of the prepulse 302 is plotted, in the case where B1=1.0.

According to the aforementioned Nyquist's theorem, it is necessary that α satisfies the following formula (12), in order to identify the variation cycle of the signal strength in the figure, using an optional flip angle α and the flip angle 2α which is doubled:

[Formula 12]

$$\alpha \leq \pi/B1 \quad (12)$$

In other words, it is necessary to select α from the flip angle range 801 (0<α≤π) as shown in FIG. 10. Here, the flip angle range 801 corresponds to ½ cycle of the signal strength variation 800.

By way of example, when 90 degrees is selected as the second flip angle α, the formula (12) is satisfied when B1 is 2.0 or less, and therefore, the cycle of the signal strength variation can be identified. However, if the B1 becomes larger than that value, the cycle of the signal strength variation cannot be identified at both flip angles, and a calculation result is a value being folded back. Therefore, when the angle of 90 degrees is selected as the second flip angle α, a value of B1 being obtainable is up to 2.0. According to the formula (12), the smaller is set the second flip angle α, the larger becomes the upper limit of the B1 value that can be obtained.

On the other hand, in the range 802 where the flip angle is close to 0 degree, a difference in signal strength between the reconstructed image obtained by the second flip angle α and the reconstructed image obtained by the third flip angle 2α becomes smaller. Accordingly, as the difference in signal strength becomes closer to the magnitude of a noise of the images, the sharpness of frequency separation is lowered due to the noise effect.

As discussed above, as the second flip angle α is set to be a smaller value, it is possible to calculate a higher B1 distribution, but calculation precision is lowered when B1 is a low value. On the other hand, as the second flip angle α is set to be a larger value, it is possible to calculate the B1 distribution more precisely when B1 is a low value, but the upper value of B1 being obtainable becomes smaller. Therefore, the second flip angle α is selected, considering in advance the possible range of B1.

Through the use of the relationship above, it is further possible to configure such that a value employed as the second flip angle α is determined depending on the B1 range being predicted. Hereinafter, a method of this modification example will be explained. In this example here, a setting of the flip angle of the prepulse 302 for each time is configured as the following; the flip angle includes zero degree, and two or more pairs of flip angles are also included, the angles being other than zero and having a relationship that one angle is twice as large as the other. Then, the segment 301 is executed at least four times, in advance. Then, a range of the B1 is specified by a predetermined computation, and according to the range thus specified, a pair of the flip angles are determined, which are used for subtraction and division together with zero degree.

Firstly, different two images are selected out of the subtraction images being created, and it is judged whether or not the B1 value is equal to or larger than a predetermined value, according to the size relationship of the absolute values of the signal strength of the target pixels in thus selected both subtraction images, thereby specifying the range of B1. Then, if it is judged that it is equal to or larger than the predetermined B1 value, a pair of smaller flip angles is determined as the pair used for the subtraction and division. If it is judged being smaller than the predetermined B1 value, a pair of larger flip angles is determined as the pair used for the subtraction and division. As the predetermined B1 value, a minimum value is selected among the B1 values which render both absolute values to be equal.

Hereinafter, using a specific example, an explanation will be made as to the RF shimming preparation process of the present embodiment performed by the RF shimming preparing part 230. It is assumed here that the count of repeating the segment is four times, and the flip angles of the prepulse 302 for those repetitions are 0 degree, 90 degrees, 180 degrees, and 360 degrees, respectively. The aforementioned pairs of the flip angles are 90 degrees and 180 degrees, and 180 degrees and 360 degrees.

Firstly, the B1 distribution measuring part 231 of the present embodiment executes the B1 distribution measurement with the conditions described above, and creates reconstructed images for the respective flip angles.

Next, the B1 distribution calculating part 232 assumes as the reference image, the reconstructed image acquired in the segment 301 that is executed with the flip angle of the prepulse 302 being set to be the minimum, i.e., 0 degree, and creates the subtraction images, respectively. When the signal strength of the target pixel in each of the reconstructed images, obtained by setting the flip angle of the prepulse 302 to be 0 degree, 90 degrees, 180 degrees, and 360 degrees, is assumed as S(0), S(90), S(180), and S(360), the absolute values of the signal strength of the target pixel in the created subtraction images become |S(90)−S(0)|, |S(180)−S(0)|, and |S(360)−S(0)|, respectively.

In this example, the values of |S(90)−S(0)| and |S(360)−S(0)| are used for judging the range of B1 value. When B1=0.8, D1=S(90)−S(0) becomes equal to D2=S(360)−S(0).

Firstly, the magnitude of |S(90)−S(0)| is compared with the magnitude of |S(360)−S(0)|. As a result, when |S(90)−S(0)|≥|S(360)−S(0)|, it is possible to assume that B1≥0.8. On this occasion, the angle α which allows calculation of a larger upper limit value, i.e., 90 degrees, is set as the second flip angle α, and the third flip angle 2α is set to be 180 degrees. Then, B1 distribution is calculated from the first subtraction image (S(90)−S(0)) and the second subtraction image (S(180)−S(0)). On the other hand, in the case where |S(90)−S(0)|<|S(360)−S(0)|, it is possible to assume that B1<0.8. On this occasion, a combination of 0 degree, 180 degrees, and 360 degree is employed, and the B1 distribution is calculated based on the second subtraction image S(180)−S(0), and the third subtraction image S(360)−S(0).

As discussed above, the segment 301 is executed at least four times with the conditions above, and by using the obtained result, a pair of the flip angles is determined. Upon specifying the range of B1 to determine the pair of flip angles, it is possible to use a reconstructed image obtained with the flip angle other than the pair to be employed. Hereinafter, an explanation will be made using a specific example.

In this example, the count for repeating the segment 301 is set to be five times, and the flip angles of the prepulse 302 for those repetitions are assumed as 0 degree, 90 degrees, 180 degrees, 270 degrees, and 360 degrees, respectively. There are two pairs of flip angles; 90 degrees and 180 degrees, and 180 degrees and 360 degrees.

Firstly, the B1 distribution measuring part 231 of the present embodiment executes the B1 distribution measurement with the conditions above, and creates reconstructed images for the respective flip angles.

Next, the B1 distribution calculating part 232 assumes as the reference image, the reconstructed image acquired by the segment 301 which is executed with setting the flip angle of the prepulse 302 to be the minimum, i.e., 0 degree, and creates the subtraction images, respectively. When the signal strength of the target pixel in each of the reconstructed images, obtained by setting the flip angle of the prepulse 302 to be 0 degree, 90 degrees, 180 degrees, 270 degrees, and 360 degrees, is assumed as S(0), S(90), S(180), S(270), and S(360), the absolute values of the signal strength of the target pixel in the created subtraction images become |S(90)−S(0)|, |S(180)−S(0)|, |S(270)−S(0)|, and |S(360)−S(0)|, respectively.

Here, when B1=1.0, the value of D1=S(90)−S(0) becomes equal to the value of D2=S(270)−S(0). In other words, when the value of B1 is 1.0, the signal strength of the target pixel in both subtraction images becomes equal. Therefore, in here, the values of |S(90)−S(0)| and |S(270)−S(0)| are used for judging the range of the B1 value. Firstly, the magnitude of |S(90)−S(0)| is compared with the magnitude of |S(270)−S(0)|.

As a result of comparison, when |S(90)−S(0)|≥|S(270)−S(0)|, it is possible to assume that B1≥1.0. Therefore, on this occasion, the angle α which allows calculation of a larger upper limit value, i.e., 90 degrees, is set to be as the second flip angle α. In other words, the third flip angle 2α is set to be 180 degrees. Then, the B1 distribution is calculated based on the first subtraction image (S(90)−S(0)), and the second subtraction image (S(180)−S(0)).

On the other hand, if |S(90)−S(0)|<|S(270)−S(0)|, it is possible to assume that B1<1.0. On this occasion, a combination of 0 degree, 180 degrees, and 360 degree is employed, and the B1 distribution is calculated based on the second subtraction image (S(180)−S(0)), and the third subtraction image (S(360)−S(0)).

As described above, according this modification example, the range of B1 is assumed based on the signal strength of thus obtained reconstructed images, and the B1 distribution is calculated by using the reconstructed images suitable for the assumed range. Accordingly, it is possible to calculate the B1 distribution by using the reconstructed images obtained by the prepulse with the flip angles being optimum in association with B1. Therefore, it is possible to calculate the B1 distribution with a higher degree of precision even in a small number of measurement times. In other words, the B1 distribution can be calculated at a similar degree of precision as the aforementioned second embodiment.

The first embodiment may also be configured as the followings; the flip angle of the prepulse 302 for each time is set in such a manner that the flip angle includes zero degree, and two or more pairs of flip angles are also included, the angles being other than zero and having a relationship that one angle is twice as large as the other, the segment 301 is executed at least four times, and then, depending on the B1 range, a pair of the flip angles used for subtraction is determined.

In each of the aforementioned embodiments, the explanations are made assuming that the static magnetic field shimming process is performed prior to the RF shimming preparation process, and thus the RF shimming preparation process is performed under the condition that the inhomogeneity of the static magnetic field has already been corrected. However, even though the static magnetic field shimming process is performed, in some cases, the inhomogeneity of the static magnetic field still remains. In such a case, it is possible to configure such that a process for correcting the transmitting sensitivity distribution caused by the static magnetic field inhomogeneity. This correction process will be explained in the following.

In the region which includes inhomogeneity in the static magnetic field distribution, the RF pulses (non selective excitation RF pulses) like the prepulse 302, which are applied without applying a gradient magnetic field may have a difference in its excitation strength, in association with a frequency difference and an excitation profile caused by the static magnetic field inhomogeneity. In the case of an RF pulse to which a slice selective gradient magnetic field is applied simultaneously with transmitting the RF pulse, like an RF pulse used in the imaging pulse sequence 301, an effect of the static magnetic field inhomogeneity appears as a location displacement in the slice direction, and it is not shown as a difference in excitation strength. In the sequence 300 of the B1 distribution measurement, since the prepulse 302 is a non selective excitation RF pulse, there occurs a transmitting sensitivity distribution (a second transmitting sensitivity distribution) rB0, due to the effect of the static magnetic field inhomogeneity.

Hereinafter, an explanation will be made as to the second transmitting sensitivity rB0.

In the region where the static magnetic field distribution includes inhomogeneity, the center frequency of the excitation profile of the RF pulse is displaced only by Δf from the center frequency, in association with the inhomogeneity degree ΔB0. The inhomogeneity degree ΔB0 and the difference Δf from the center frequency are expressed by the following formula (13). Here, γ represents a gyromagnetic ratio:

[Formula 13]

$$\Delta f = 2\pi \cdot \gamma \cdot \Delta B0 \quad (13)$$

Figure 11A:
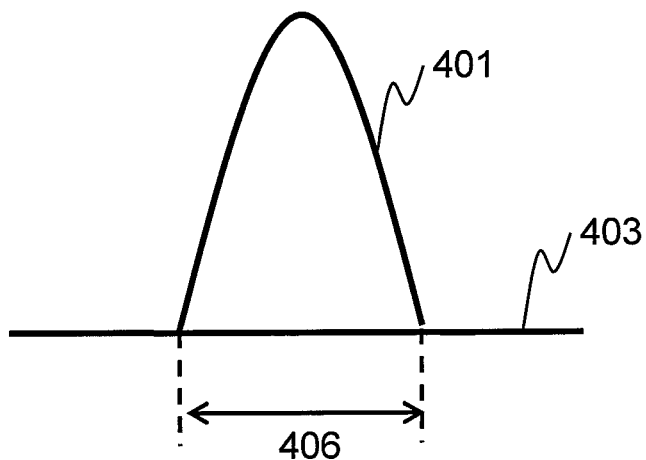
FIG. 11A illustrates an irradiation waveform of the RF pulse.
Figure 11B:
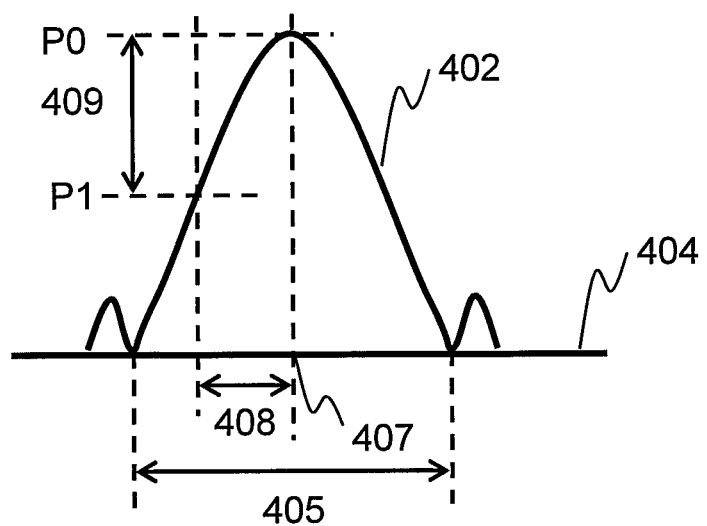
FIG. 11B illustrates an excitation profile.

When the center frequency of the excitation profile is displaced only by Δf, a difference occurs in the excitation strength. FIG. 11A is a schematic view of a transmission waveform 401 of the RF pulse. FIG. 11B is a schematic view of an excitation profile 402 of the RF pulse. The reference numeral 403 of FIG. 11A indicates a time axis, and the reference numeral 404 of FIG. 11B indicates a frequency axis. The excitation profile 402 is obtained by subjecting the transmission waveform 401 to the Fourier transform, and the transmission band 405 is determined by the application time 406 of the RF pulse. The center frequency f0 (407) of the excitation profile 402 coincide with the transmission frequency of the RF pulse. The vertical axis of the excitation profile 402 indicates the excitation strength of the excitation profile. Therefore, there occurs a difference in excitation strength 409, in association with a difference in frequency 408 from the center frequency 407 of the excitation profile 402, which is caused by the static magnetic field inhomogeneity degree ΔB0.

On this occasion, if the excitation strength at the center frequency of the excitation profile is assumed as P0, and the excitation strength at the frequency being different from the center frequency by Δf is assumed as P1, the second transmitting sensitivity rB0 of a pixel associated with a region having the inhomogeneity degree ΔB0 which causes the frequency difference Δf, is expressed by the following formula (14):

[Formula 14]

$$rB0 = P1/P0 \quad (14)$$

The transmitting sensitivity B1 of a pixel in such a region as described above contains components as the following; a first transmitting sensitivity B1o generated by the transmitting sensitivity inhomogeneity of the transmit RF coil, and the second transmitting sensitivity rB0 generated by the excitation profile of the RF pulse and the static magnetic field inhomogeneity. In other words, B1=B1o×rB0. Therefore, the transmitting sensitivity B1o originally intended to be calculated is obtained by dividing B1 by rB0. It is to be noted that the aforementioned embodiments are examples in the case where the static magnetic field inhomogeneity is almost solved, i.e., in the case where rB0=1.0 and B1=B1o.

The B1 distribution calculating part 232 in the RF shimming preparing part 230, firstly transforms the static magnetic field distribution after the inhomogeneity has been corrected by B0 shimming, into a distribution having a frequency difference Δf, being a difference from the center frequency f0. This is performed by using the aforementioned formula (13).

Next, the B1 distribution calculating part 232 calculates from the excitation profile of the RF pulse used in the prepulse 302, the excitation strength P0 at the center frequency and the excitation strength P1 in association with the frequency difference Δf. It is possible to configure as the following for calculating the excitation strength P1; a relationship between the frequency difference Δf and the excitation strength P1 is held in advance as a data table, and the excitation strength P1 which is held in association with the frequency difference Δf is extracted. It is alternatively possible to configure such that a function is prepared in advance for calculating the excitation strength P1 assuming the frequency difference Δf as a variable, and the calculation is performed by using this function.

Thereafter, the B1 distribution calculating part 232 calculates rB0 according to the formula (14). Then, B1 for each pixel being calculated in each of the aforementioned embodiments is divided by rB0, thereby calculating B1o.

On this occasion, in the phase difference and amplitude ratio calculating process, the phase difference and amplitude ratio calculating part 233 uses thus calculated B1o instead of B1, and calculates the inter-channel phase difference and amplitude ratio of the RF pulses irradiated by the respective channels 150.

In each of the aforementioned embodiments, the imaging sequence 303 used in the measurement for calculating the B1 distribution can be set to any pulse sequence. It is to be noted here that a high-speed imaging sequence, such as EPI (Echo Planar Imaging) and RSSG (RF Spoiled-Steady state Acquisition with Rewound Gradient Echo) is preferably set as the pulse sequence. This is because such high-speed imaging sequence allows a reduction of the imaging time.

It is further preferable that TI is set as short as possible, and in the imaging sequence 303, a nuclear magnetic resonance signal at the center of the k-space is measured at the timing as early as possible. This is because those settings above may allow the prepulse 302 to have a large impact on the nuclear magnetic resonance signal acquired in the imaging sequence 303. Accordingly, the amplitude of the signal strength variation of the image expressed by the formula (2) becomes larger, and the precision level in calculating the B1 distribution is enhanced.

Furthermore, in the MRI apparatus according to each of the aforementioned embodiments, the non selective excitation type prepulse 302 is used as the prepulse 302 of the sequence 300 that is employed for the B1 distribution measurement. As discussed above, in each of the aforementioned embodiments, since the prepulse 302 is the non selective excitation type, multi-slice imaging is also applicable to the imaging sequence 303.

On the other hand, it is further possible to configure such that a selective excitation type prepulse is used as the prepulse 302, such prepulse applying a slice selective gradient magnetic field. On this occasion, the prepulse to be used is configured as an RF pulse being settable to any flip angle, and a gradient magnetic field is continuously applied for establishing saturated transverse magnetization. As described above, by setting the selective excitation type prepulse as the prepulse to be used, even in the state where static magnetic field inhomogeneity exists, it is not necessary to correct the transmitting sensitivity distribution caused by the static magnetic field inhomogeneity. In this case, the imaging sequence 303 is limited to single slice imaging. On this occasion, if multiple-slice imaging is performed, a multi-slice imaging structure is established in the segment 301 which also includes the prepulse 302.

Generally, it is preferable to set TD to be a shorter time, since the time required for the B1 distribution measurement is reduced. However, the measurement for calculating the B1 distribution in each of the aforementioned embodiments is performed based on the premise that there is no interference between the prepulses 302. In other words, it is assumed that longitudinal magnetization is in the state of completely recovered between TDs. Therefore, TD needs a certain length. In each of the aforementioned embodiments, considering both situations above, an optimum TD is decided from T1 values which contribute to the entire B1 homogeneity in a healthy living body.

If there exists ascites fluid, or the like, the T1 value becomes longer to contribute to the entire B1 homogeneity, and therefore it is preferable to set the TD to be longer than the value set in a healthy living body. Therefore, in the MRI apparatus in each of the aforementioned embodiments, if there are found many tissues having long T1, such as ascites fluid, in a scout image of the reference scan, it is possible to configure such that TD is automatically set to be longer, or promoting the operator for setting the TD to be longer, as a recommended matter. With this configuration as described above, even a region including ascites fluid, or the like, is a imaging target, it is possible to calculate B1 with a high degree of precision.

As explained above, according to each of the aforementioned embodiment, it is possible to easily calculate the B1 distribution at high speed and with a high degree of precision. Therefore, the imaging time can be reduced while keeping the image quality. On the other hand, a high quality image can be obtained within a short time. In other words, each of the aforementioned embodiments allows the measurement of the B1 distribution simply and at high speed, and it is possible to execute examination while reducing image non-uniformity, within a short time.

EXPLANATION OF REFERENCES

100: MRI apparatus, 101: magnet, 102: gradient coil, 103: transmission coil, 104: reception coil, 105: shim coil, 110: sequencer, 112: gradient power supply, 113: RF pulse generator, 114: receiver, 115: shim power supply, 120: information processor, 121: storage unit, 122: display unit, 123: input unit, 130: subject, 140: table, 150: channel, 210: reference measuring part, 220: static magnetic field shimming part, 230: RF shimming preparing part, 231: B1 distribution measuring part, 232: B1 distribution calculating part, 233: phase difference and amplitude ratio calculating part, 234: phase difference and amplitude ratio setting part, 240: main scan part, 250: display processor, 300: sequence, 301: segment, 302: prepulse, 303: imaging sequence, 304: measurement timing, 305: TI, 306: TD, 401: irradiation waveform, 402: excitation profile, 403: time axis, 404: frequency axis, 405: transmission band, 406: application time, 407: center frequency, 408: difference in frequency, 409: difference in excitation strength, 701: signal strength graph, 702: plot result of absolute value of subtraction image, 703: approximate function, 704: maximum value, 801: flip angle range, 802: flip angle range

What is claimed is:

1. A magnetic resonance imaging apparatus, comprising,
    a static magnetic field forming unit for forming a static magnetic field in a space where a subject is placed,
    a gradient magnetic field applying unit for applying a gradient magnetic field to the subject,
    a radio frequency magnetic field applying unit having a transmission coil with multiple channels and applying a radio frequency magnetic field to the subject,
    a signal receiving unit for receiving a nuclear magnetic resonance signal generated from the subject,
    a measurement control unit for controlling according to a predetermined imaging sequence, operations of the gradient magnetic field applying unit, the radio frequency magnetic field applying unit, and the signal receiving unit, thereby performing measurement, and
    a transmitting sensitivity shimming preparing unit for calculating inter-channel phase difference and amplitude ratio of RF pulses applied from the channels respectively, so as to correct inhomogeneity of a transmitting sensitivity distribution of the transmission coil,
    the transmitting sensitivity shimming preparing unit further comprising,
    a transmitting sensitivity measuring unit for repeatedly executing an imaging sequence to which a prepulse is added while applying the prepulse at different flip angles, thereby acquiring multiple reconstructed images for the respective flip angles of the prepulse, with respect to each of the channels of the transmission coil,
    a transmitting sensitivity distribution calculating unit for determining a reference image from the multiple reconstructed images, calculating a subtraction image between the reference image and each of the reconstructed images other than the reference image, with respect to each of the channels of the transmission coil, and calculating the transmitting sensitivity distribution by using the subtraction images being calculated,
    a phase difference and amplitude ratio calculating unit for calculating independently, inter-channel phase difference and amplitude ratio of the RF pulses transmitted to the respective channels of the transmission coil, based on the transmitting sensitivity distribution being calculated, and
    a phase difference and amplitude ratio setting unit for setting the phase difference and the amplitude ratio being calculated, to the measurement control unit, and
    the measurement control unit controlling the radio frequency magnetic field applying unit to apply the RF pulses with the phase difference and the amplitude ratio being set, from the respective channels of the transmission coil.

2. The magnetic resonance imaging apparatus according to claim 1, wherein,
    the transmitting sensitivity measuring unit repeatedly executes the imaging sequence at least three times, and the transmitting sensitivity distribution calculating unit further performs division between the subtraction images being calculated, and calculating the transmitting sensitivity distribution by using a result of the division.

3. The magnetic resonance imaging apparatus according to claim 1, wherein,
    the flip angle of the prepulse includes zero degree.

4. The magnetic resonance imaging apparatus according to claim 3, wherein,
    the flip angle of the prepulse includes a first angle other than zero degree, and an angle being twice as large as the first angle.

5. The magnetic resonance imaging apparatus according to claim 3, wherein,
    the transmitting sensitivity measuring unit repeatedly executes the imaging sequence at least four times, and the flip angle of the prepulse includes at least two pairs of flip angles other than zero degree, the pair having a relationship that one angle being twice as large as the other angle.

6. The magnetic resonance imaging apparatus according to claim 5, wherein,
    the transmitting sensitivity distribution calculating unit determines, based on signal strength with respect to each pixel of the subtraction images, a range of the transmitting sensitivity of the pixel, and determines the reconstructed images for calculating the transmitting sensitivity distribution in association with the range being determined.

7. The magnetic resonance imaging apparatus according to claim 3, wherein,
    the transmitting sensitivity distribution calculating unit assumes as the reference image, the reconstructed image acquired by the imaging sequence that is executed setting the flip angle to zero degree.

8. The magnetic resonance imaging apparatus according to claim 1, further comprising a static magnetic field shimming unit for correcting inhomogeneity of the static magnetic field, wherein,
    the transmitting sensitivity shimming preparing unit corrects the inhomogeneity of the transmitting sensitivity distribution, in the state where the inhomogeneity of the static magnetic field has been corrected by the static magnetic field shimming unit.

9. The magnetic resonance imaging apparatus according to claim 8, wherein,
    the transmitting sensitivity distribution calculating unit further comprises a correction value calculating unit for calculating as a correction value, an effect on the transmitting sensitivity distribution caused by the inhomogeneity of the static magnetic field, and
    the transmitting sensitivity distribution calculating unit further uses the correction value being calculated by the correction value calculating unit, so as to calculate the transmitting sensitivity distribution.

10. The magnetic resonance imaging apparatus according to claim 9,
    the correction value calculating unit calculates the correction value, from a static magnetic field distribution after being corrected by the static magnetic field shimming unit and a transmission band of the prepulse being applied.

11. A transmitting sensitivity distribution calculating method for calculating a transmitting sensitivity distribution of multiple channels of a transmission coil in a magnetic resonance imaging apparatus, for applying RF pulses to a subject placed in a static magnetic field, the method comprising steps of, repeatedly executing an imaging sequence to which a prepulse is added while applying the prepulse at different flip angles, thereby acquiring multiple reconstructed images for the respective flip angles of the prepulse, with respect to each of the channels, and determining a reference image from the multiple reconstructed images, calculating a subtraction image between the reference image and each of the reconstructed images other than the reference image, with respect to each of the channels, and calculating a transmitting sensitivity distribution by using the calculated subtraction images.

* * * * *